United States Patent [19]
Allen et al.

[11] Patent Number: 6,099,812
[45] Date of Patent: Aug. 8, 2000

[54] STERILIZATION TRAY WITH REMOVABLE INSTRUMENTATION WALL

[75] Inventors: Kraig H. Allen; Thomas J. Bussell, both of Warsaw, Ind.; Stephen L. Peterson, Wayzata, Minn.; Jason M. Winterrowd, South Whitley, Ind.

[73] Assignee: Paragon Medical, Inc., Pierceton, Ind.

[21] Appl. No.: 09/099,261

[22] Filed: Jun. 18, 1998

[51] Int. Cl.[7] .................................................. A61L 2/00
[52] U.S. Cl. ...................... 422/300; 206/370; 206/438; 220/529; 220/735; 422/297
[58] Field of Search ................... 422/297, 300; 206/363, 365, 370, 438, 439; 220/676, 505, 735, 529

[56] References Cited

U.S. PATENT DOCUMENTS

| | | | |
|---|---|---|---|
| 4,762,688 | 8/1988 | Berry, Jr. ................................ | 422/297 |
| 5,183,643 | 2/1993 | Nichols .................................. | 422/297 |
| 5,407,648 | 4/1995 | Allen et al. ............................ | 422/297 |
| 5,441,709 | 8/1995 | Berry, Jr. ................................ | 422/297 |
| 5,518,115 | 5/1996 | Latulippe .............................. | 422/300 |
| 5,525,314 | 6/1996 | Hurson .................................. | 422/300 |
| 5,540,901 | 7/1996 | Riley ..................................... | 422/300 |
| 5,628,970 | 5/1997 | Basile et al. .......................... | 422/300 |

*Primary Examiner*—Krisanne Thornton
*Attorney, Agent, or Firm*—Baker & Daniels

[57] ABSTRACT

A sterilization tray for supporting medical instrumentation during the sterilization process. The tray includes a base having a perforated bottom wall to allow the passage of sterilization steam into the tray. A removable floor is fitted into the base and supported spacedly above the base bottom wall. The floor also includes perforations to allow for the passage of sterilization steam into the tray and above the instrumentation therein. One or more instrument holders are supported by the floor, extending upwardly from the floor in a direction opposite the location of the base bottom wall. The instrument holders can be removed from the floor with the floor being removed from the base, reversed in orientation and fitted into the base in its spaced relationship from the base bottom wall. The instrument holders are then repositioned upon the floor, extending upwardly from the opposite side of the floor.

9 Claims, 6 Drawing Sheets

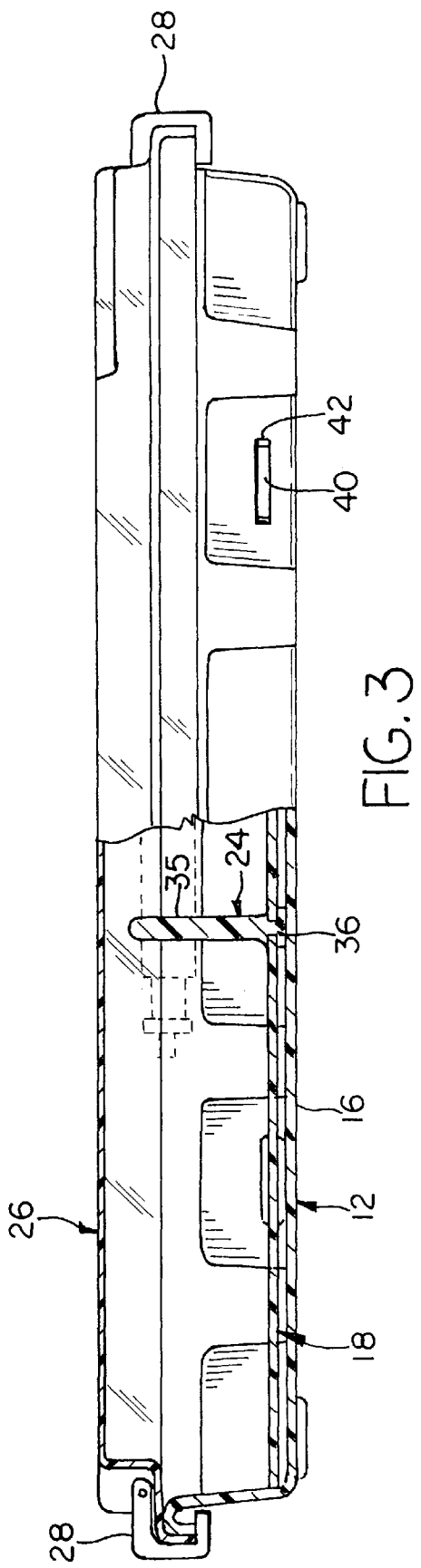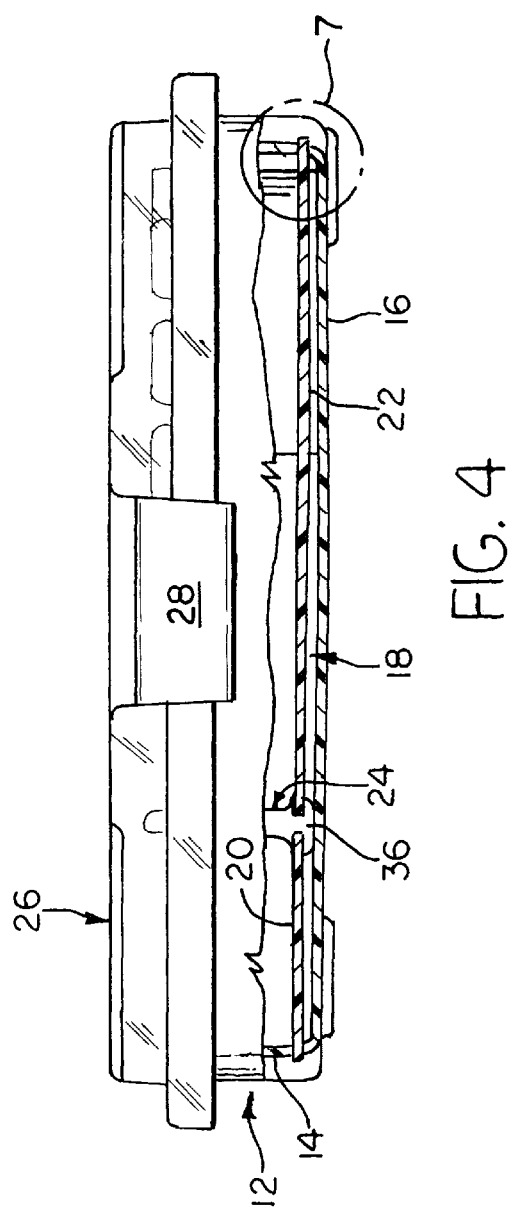

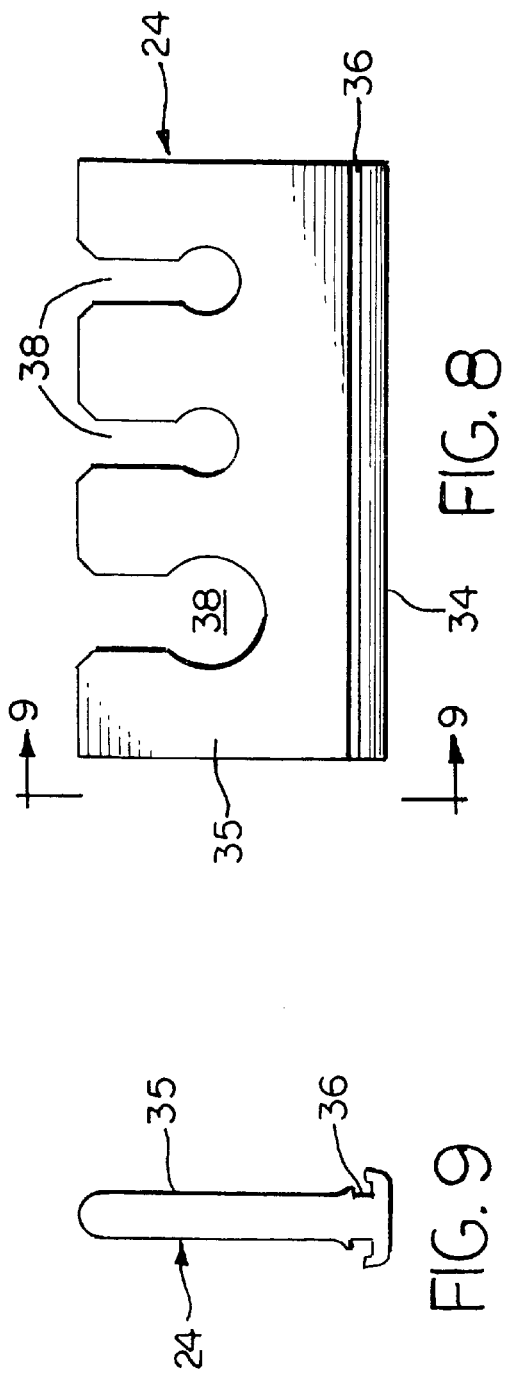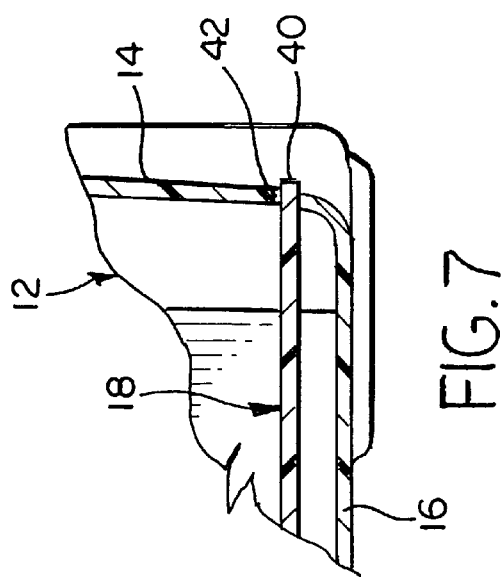

STERILIZATION TRAY WITH REMOVABLE INSTRUMENTATION WALL

SUMMARY OF THE INVENTION

This invention relates to a sterilization tray for medical instrumentation and will have application to a tray which is designed to accommodate various types and layouts of instrumentation by way of a reversible support floor.

The sterilization tray of this invention is designed to provide a convenient and economical manner in which to accommodate various types and layouts of medical instrumentation. In this invention, the tray includes a base with a perforated bottom wall to allow the passage of sterilization steam or similar matter. A floor is provided which is fitted into the base and is supported spacedly above the base bottom wall. The floor also has perforations to allow the passage of the sterilization steam or similar matter. The floor is adapted to be removed from the base and inverted and replaced at the option of the user. Removably mounted to the exposed side of the floor when it is within the base are instrumentation holders. A cover is provided for covering the base and enclosing the floor with its holders and instrumentation during the sterilization process.

Accordingly, it is an object of this invention to provide a sterilization tray which is for medical instrumentation and which is of simplified usage.

Still another object of this invention is to provide a sterilization tray which is for medical instrumentation and which is of economical construction.

A further object of this invention is to provide a sterilization tray for medical instrumentation which can accommodate in various orientations instrument holders with appropriate labeling.

Other objects of this invention will become apparent upon reading the following description.

BRIEF DESCRIPTION OF THE DRAWINGS

A preferred embodiment has been chosen wherein:

FIG. 3 is a side view of the tray with portions removed for illustrative purposes.

FIG. 4 is an end view of the tray with portions removed for illustrative purposes.

FIG. 7 is an enlarged partial sectional view of that portion of the tray shown within broken line circle 7 of FIG. 4.

FIG. 8 is a side view of an instrument holder of the tray.

FIG. 9 is an end view of the instrument holder.

DESCRIPTION OF THE PREFERRED EMBODIMENT

Figure 1:
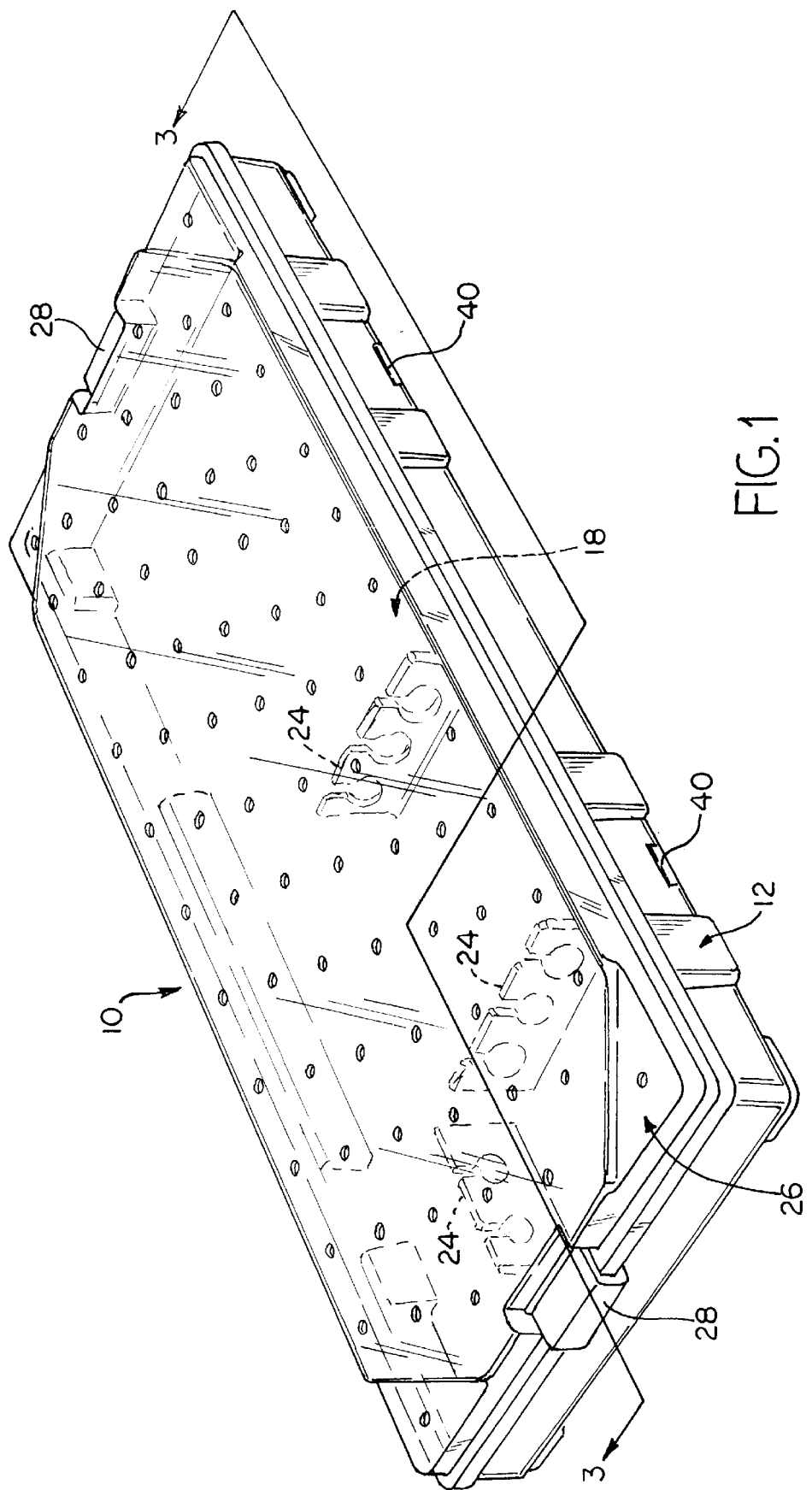
FIG. 1 is a perspective view of the tray in assembled form.
Figure 2:
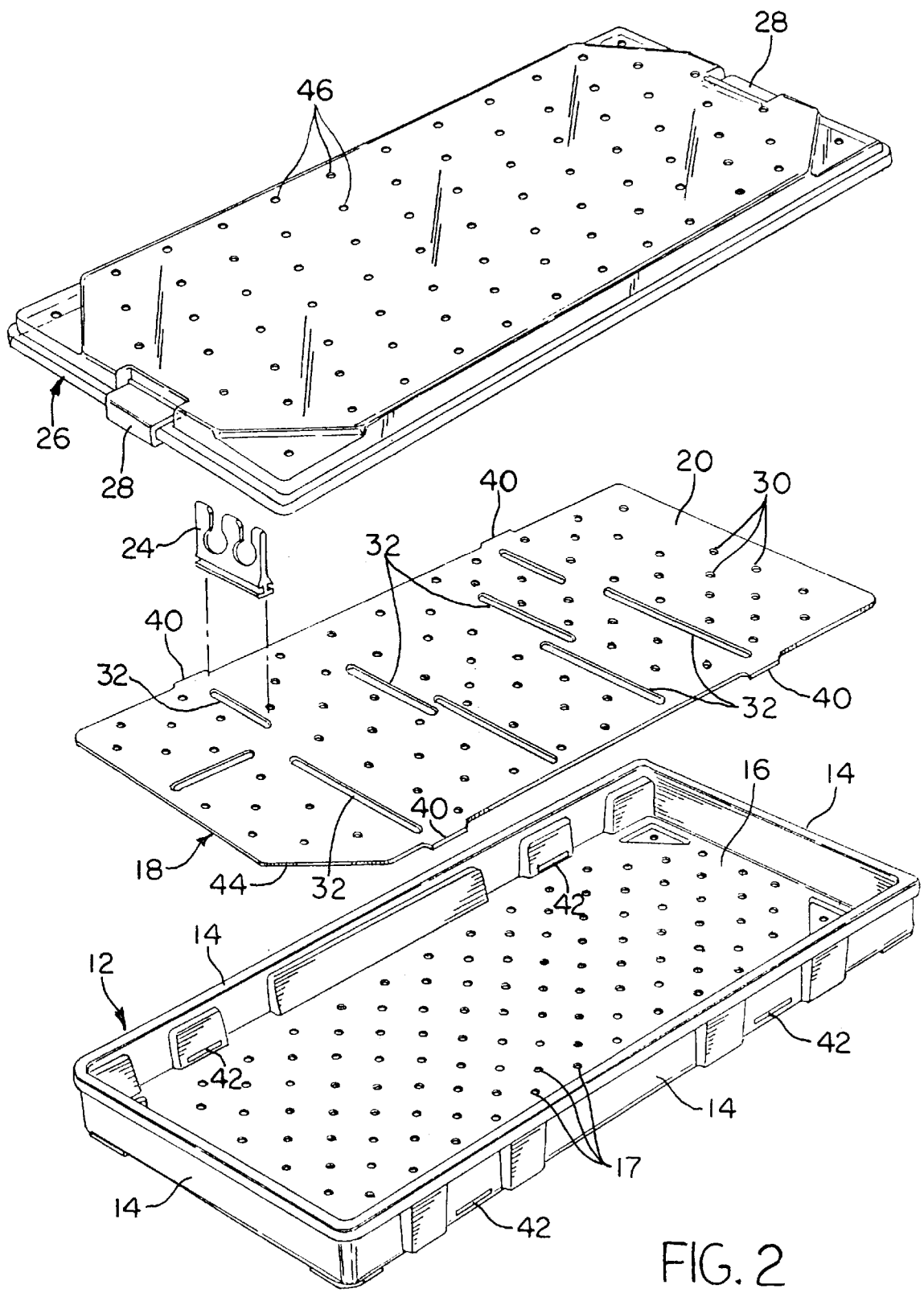
FIG. 2 is a view of the tray with its components shown in exploded form.
Figure 5:
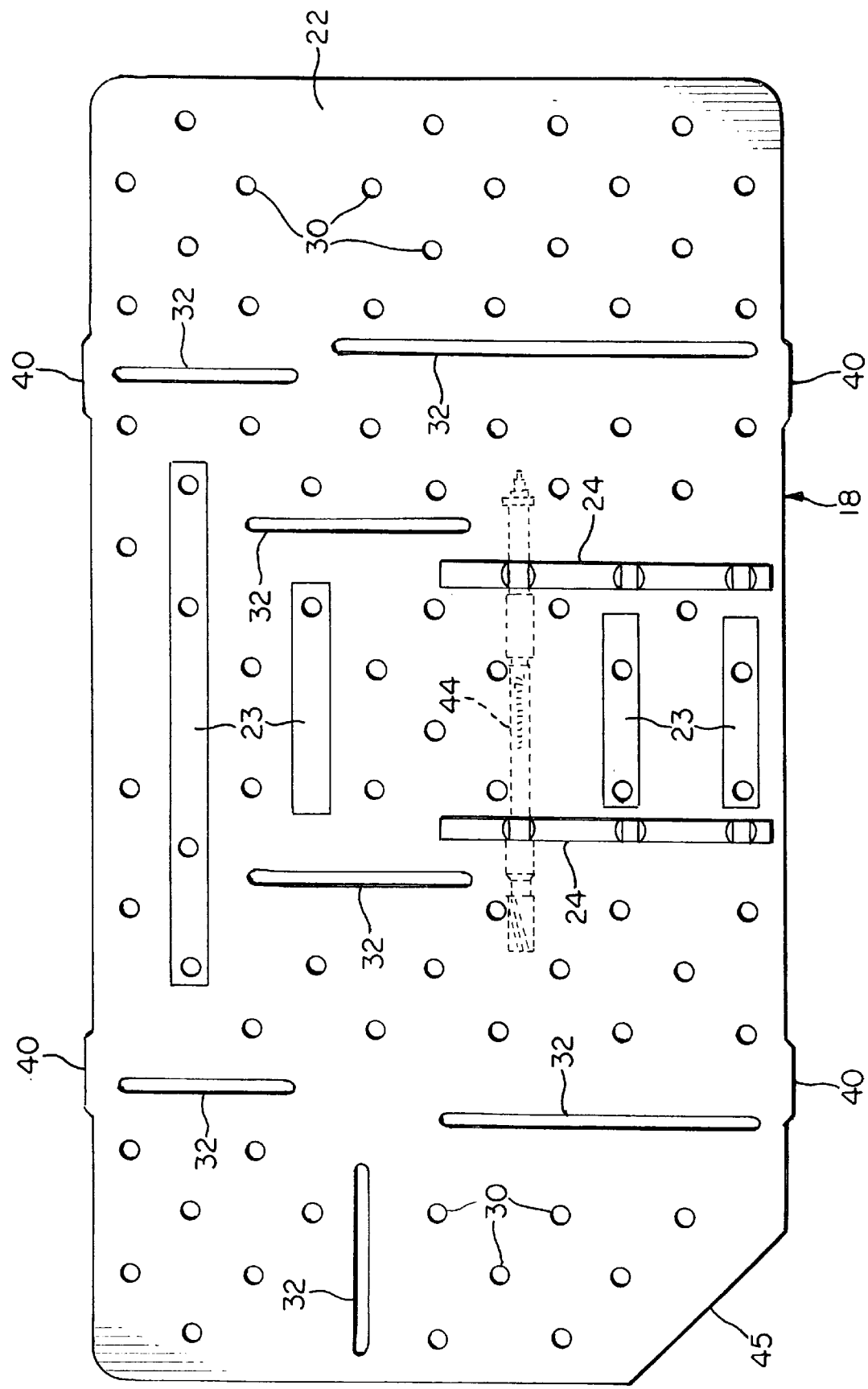
FIG. 5 is a top view of one side of the removable floor of the tray.
Figure 6:
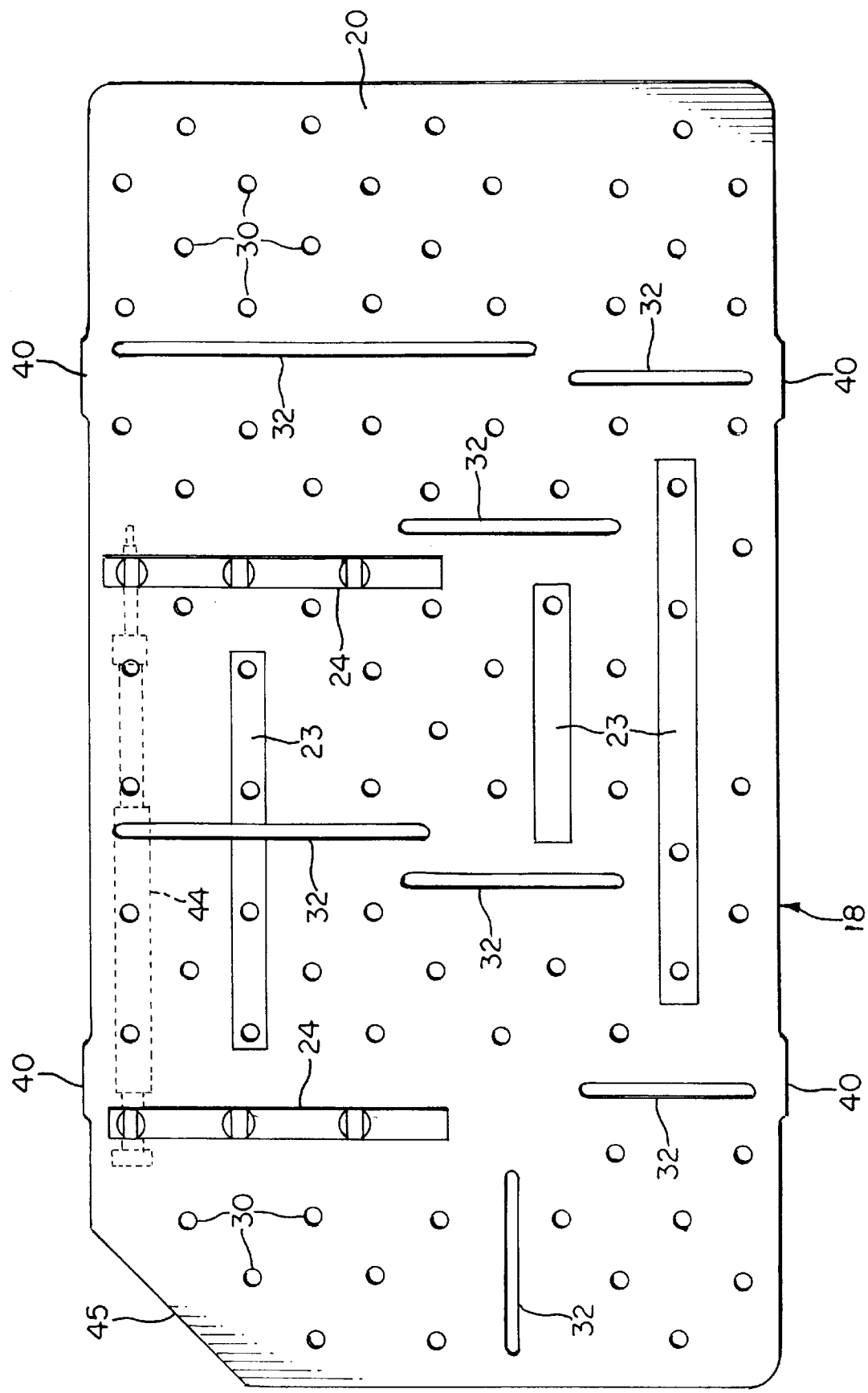
FIG. 6 is a top view of the opposite side of the removable floor of the tray.

The preferred embodiment illustrated is not intended to be exhaustive or to limit the invention to the precise form disclosed. It is chosen and described in order to best explain the invention and its application and practical use to enable others skilled in the art to best utilize the invention.

As shown in the figures tray 10, which is preferably formed of a plastic material but which may be formed of a metal composition capable of repeated heated sterilization, includes a base 12, a floor 18, and a cover 26. Base 12 includes enclosing side walls 14 and a bottom wall 16. Bottom wall 16 includes a plurality of perforations or holes 17 to allow for the passage of sterilization material such as steam into the tray.

Floor 18 of tray 10 has opposite sides 20, 22. Floor 18 also includes a plurality of perforations or holes 30 to allow the passage of the sterilization matter such as steam as well as a plurality of specifically oriented slots 32. Slots 32 are provided to accommodate a plurality of the instrument holders 24. Each holder 24 may vary in configuration but preferably includes a foot 34 separated from the general body 35 of the holder by neck 36. Body 35 of each holder accommodates one or more vertically oriented slots 38 into which the medical instrument 44 is seated when within tray 10. Holders 24 are preferably formed of a pliable shaped retaining material which allows them to be removably secured to floor 18 by having the foot 34 of each holder pressed through a slot 32 in the floor with the foot extending below one side 20 or 22 of the floor and with the body 35 extending above the other side 20 or 22 of the floor. Each side 20, 22 of floor 18 preferably includes a plurality of labels 23 which are strategically positioned relative to slots 32 and which serve when provided with proper indicia to identify the instruments carried by holders 24 when they are secured to floor 18 within slots 32.

Floor 18 includes at tabs 40 opposite edges which are fitted into accommodating slots 42 formed in side walls 14 of its base 12 above bottom wall 16. Base 12 and floor 18 are sufficiently flexible to allow side walls 14 of base 12 to be flexed to allow the floor to be snap fitted at its tabs 40 into slots 32 and thus supported spacedly above bottom wall 16 of the base as illustrated. One corner 45 of floor 18 is beveled, thus providing an opening into the base to accommodate one's fingers when the floor is to be pried in a flexed manner from securement to base 12 by the removal of tabs 40 from base slots 42.

Cover 26, which is preferably transparent to allow a viewing of the instrumentation held within tray 10, covers base 12 at its sides 14, enclosing floor 18, holders 24 and any instruments 44 (shown for illustrative purposes in broken lines) within tray 10. Cover 26 is preferably secured to base 12 by latches 28 which are located at opposite ends of the cover. The cover is perforated by holes 46 to also allow for the passage of the sterilization material through the tray.

When floor 18 is secured within base 12, the floor is retained in its spaced relationship above bottom wall 16 of base 12 by feet 34 of holders 24 which serves as supporting spacers. Holder feet 34 rest upon bottom wall 16 of the base, thereby keeping the floor 18 suspended above bottom wall 16 to allow for complete and thorough sterilization by the passage of sterilization matter through perforations 17, 30, and 46 of the base, floor, and cover respectively onto the instruments.

Holders 24 prior to the insertion of floor 18 into base 12 can be fitted into floor slots 32 at one side 20, 22 of the floor with neck 36 of each holder being restrictively secured within a slot and foot 34 extending to one side and body 35 extending upwardly from the other side of the floor. Slots 32 are oriented so as to permit the holders to be positioned in various locations relative to the floor to allow for the accommodation of various types of instruments. When it is desired for tray 10 to accommodate different types or layouts of instrumentation, floor 18 need only be removed from base 12, and holders 24 reoriented into selected slots 32 from the opposite side of the floor. Floor 18 is then fitted back into base 12 in an inverted orientation. In this manner by having floor 18 invertible, various instrumentation may be retained by a single tray depending upon which side 20, 22 is uppermost within base 12 and the positions of holders 24 which are carried by the exposed side of the floor.

The above invention is not to be limited to the details above given but may be modified within the scope of the appended claims.

What we claim is:

1. A sterilization tray for medical instruments comprising a base having enclosed side walls and a bottom wall, said bottom wall being perforated to allow the passage of sterilization matter into the tray, a floor having opposite sides removably fitted into said base and supported spacedly above said base bottom wall with one of said floor sides oppositely facing the bottom wall, said floor bing perforated to allow for the passage of sterilization matter into the tray, an instrument holder carried by said floor and extending from the other of said floor sides to accommodate at least one of said medical instruments, and a removable cover applied over said base at said base side walls enclosing said floor within said tray, said floor being reversible in orientation relative to said base to position either of said floor sides oppositely located from said base bottom wall.

2. The tray of claim 1 wherein said instrument holder includes a body part extending above said floor and a foot part extending below said floor, said foot part engaging said base bottom wall.

3. The tray of claim 2 wherein said floor has an opening therein, said holder fitted in said opening.

4. The tray of claim 3 and a second said holder, said floor having a second said opening therein, and said second said holder fitted into said second said opening.

5. The tray of claim 4 wherein each said holder includes a slotted part for accommodating one of said medical instruments.

6. The tray of claim 3 wherein said holder includes a neck part between its said body part and said foot part, said neck part being restrictively located in said floor opening.

7. The tray of claim 1 wherein said cover is perforated to allow for the passage of sterilization matter through said tray.

8. The tray of claim 1 wherein said floor includes a gripping part to accommodate the floor's removal from said base.

9. The tray of claim 1 wherein said floor includes oppositely extending laterally directed tabs, said base side walls having slotted openings therein spaced above said base bottom wall, said floor tabs fitted into said base slotted openings.

* * * * *